US011231407B2

(12) United States Patent
Price et al.

(10) Patent No.: US 11,231,407 B2
(45) Date of Patent: Jan. 25, 2022

(54) SYSTEM AND METHOD FOR GRAPHENE-STRUCTURE DETECTION DOWNHOLE

(71) Applicant: Halliburton Energy Services, Inc., Houston, TX (US)

(72) Inventors: James M. Price, Cypress, TX (US); Christopher Michael Jones, Katy, TX (US); Jian Li, Bellaire, TX (US); Julia Golovko, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 155 days.

(21) Appl. No.: 16/578,559

(22) Filed: Sep. 23, 2019

(65) Prior Publication Data

US 2021/0088497 A1 Mar. 25, 2021

(51) Int. Cl.
*G01N 33/24* (2006.01)
*E21B 49/08* (2006.01)
*E21B 49/10* (2006.01)
*G01N 21/65* (2006.01)
*G01N 23/2273* (2018.01)

(52) U.S. Cl.
CPC .......... *G01N 33/24* (2013.01); *E21B 49/081* (2013.01); *E21B 49/086* (2013.01); *E21B 49/088* (2013.01); *E21B 49/10* (2013.01); *G01N 21/65* (2013.01); *G01N 23/2273* (2013.01); *E21B 49/0875* (2020.05)

(58) Field of Classification Search
CPC .. E21B 49/081; E21B 49/086; E21B 49/0875; E21B 49/088; E21B 49/10; G01N 21/65; G01N 23/2273; G01N 33/24

USPC ............................................................ 356/301
See application file for complete search history.

(56) References Cited

U.S. PATENT DOCUMENTS

| 3,345,137 | A | * | 10/1967 | McAuliffe | ............ | G01V 9/007 |
|  |  |  |  |  |  | 436/29 |
| 3,561,546 | A | * | 2/1971 | Craig | ....................... | G01N 1/12 |
|  |  |  |  |  |  | 175/5 |
| 7,087,555 | B2 |  | 8/2006 | Halliday et al. | | |
| 8,183,180 | B2 |  | 5/2012 | Tour et al. | | |
| 8,760,968 | B2 | * | 6/2014 | Dai | ....................... | G01V 1/3808 |
|  |  |  |  |  |  | 367/73 |
| 9,377,449 | B2 |  | 6/2016 | Tour et al. | | |

(Continued)

FOREIGN PATENT DOCUMENTS

| EP | 0860715 | 6/2006 |
| JP | 2013-527926 | 7/2013 |
| WO | 2018-160259 | 9/2018 |

OTHER PUBLICATIONS

International Search Report and Written Opinion for Application No. PCT/US2019/052896 dated Jun. 22, 2020.

(Continued)

*Primary Examiner* — Sunghee Y Gray
(74) *Attorney, Agent, or Firm* — John Wustenberg; C. Tumey Law Group PLLC (57) ABSTRACT

A method may comprise sampling a wellbore fluid; analyzing the wellbore fluid and determining a presence of a graphene-like substrate, a concentration of the graphene-like substrate, or both, in the wellbore fluid; and correlating the presence and the concentration of the graphene-like substrate to at least one subterranean formation characteristic.

18 Claims, 5 Drawing Sheets

(56) References Cited

U.S. PATENT DOCUMENTS

| | | |
|---|---|---|
| 9,449,743 B2 | 9/2016 | Tour et al. |
| 9,920,233 B2 | 3/2018 | Husein et al. |
| 9,988,901 B2* | 6/2018 | Rowe .................... E21B 49/086 |
| 2008/0133193 A1 | 6/2008 | Gdanski et al. |
| 2009/0071239 A1 | 3/2009 | Rojas et al. |
| 2012/0245058 A1* | 9/2012 | Monteiro ................ C09K 8/032 |
| | | 507/110 |
| 2013/0075093 A1 | 3/2013 | Van Hal et al. |
| 2014/0357788 A1* | 12/2014 | Shene ..................... C08K 3/042 |
| | | 524/599 |
| 2016/0340570 A1* | 11/2016 | Salla ....................... C09K 8/516 |
| 2017/0167257 A1* | 6/2017 | Rowe .................... E21B 49/088 |
| 2017/0327729 A1* | 11/2017 | Salla ........................ C09K 8/68 |
| 2017/0329044 A1 | 11/2017 | DiFoggio |
| 2019/0129056 A1* | 5/2019 | Rasmus ................... G01V 3/30 |
| 2020/0340329 A1* | 10/2020 | Al-Mulhem ........... C09K 8/508 |

OTHER PUBLICATIONS

Jamrozik, Alexsandra, Graphene and Graphene Oxide in the Oil and gas industry, AGH Drilling, Oil, Gas, vol. 34, 2017.

Marko Spasenovic, Graphene for Oil Exploration, Dec. 16, 2013.

* cited by examiner

SYSTEM AND METHOD FOR GRAPHENE-STRUCTURE DETECTION DOWNHOLE

BACKGROUND

The oil and gas industry typically conducts comprehensive evaluation of underground hydrocarbon reservoirs prior to their development. Formation evaluation procedures generally involve collection of formation fluid samples for analysis of their hydrocarbon content, estimation of the formation permeability, and directional uniformity, determination of the formation fluid pressure, and many others. Measurements of such parameters of the geological formation are typically performed using many devices including downhole formation testing tools.

In a typical operation, formation-testing tools operate as follows. Initially, the tool is lowered on a wireline into the borehole to a desired depth and the probes for taking samples of the formation fluids are extended into a sealing contact with the borehole wall. Formation liquid is then drawn into the tool through inlets, and the tool may perform various tests of the formation properties, as known in the art. There is a need to provide systems and methods to further evaluate the samples of formation fluids to identify chemical species present in the formation and use such identification for characterizing one or more formation characteristics.

BRIEF DESCRIPTION OF THE DRAWINGS

These drawings illustrate certain aspects of some of the examples of the present disclosure, and should not be used to limit or define the disclosure.

DETAILED DESCRIPTION

The present disclosure relates to subterranean operations and, more particularly, the embodiments disclosed herein provide methods and systems for characterizing and determining downhole fluid constituents with a graphene or graphene-like substrate or backbone structure in a reservoir formation. Further, the disclosure may relate to defining a graphene-like compositional gradient and embodiments provide methods and systems for defining the graphene compositional gradient. As referenced herein, the term "graphene-like compositional gradient" or "graphene-like gradient" is the composition or quantity of the graphene-like substrate as a function of depth. Notably, graphene may be characterized by a large specific surface area and a unique absorption capacity for chemical compounds. Therefore, substrates having graphene or graphene-like qualities may be demonstrated useful for various desirable characteristics of subterranean formations, including, but not limited to, characterizing hemodynamic formations, reservoir architecture, reservoir/formation interval productivity, reservoir charging mechanisms, filling histories and/or oil and gas migration pathways. As referenced in this disclosure, the term "graphene-like" includes, but is not limited to, characteristics such as IR Raman spectra or X-Ray photoelectron spectroscopy, wherein unique spectroscopic signatures may be identifiable, wherein the spectrographic peak may range from at least about 2700 cm-1 up to at least about 3400 cm-1 for a Raman shift, or wherein the spectrographic peak may range from at least about 284 eV up to at least about 300 eV for X-Ray photoelectron spectroscopy. Moreover, a structural component may comprise a two-dimensional hexagonal lattice structure, which is characteristic of traditional graphene. Characteristics may further include other allotropes of carbon, wherein the substrate has a three-dimensional (3D) component, such as molecular thickness.

Oil and gas containing subterranean formations may contain a wide variety of hydrocarbons ranging from simple hydrocarbons such as methane, ethane, and propane up to complex polycyclic aromatic hydrocarbons. The composition of produced fluids from a subterranean formation may vary over time as the formation is drained. For one subterranean formation, relatively lighter hydrocarbons may be produced early on in well life and the fraction of relatively lighter hydrocarbons in produced fluids may decrease as the well matures. Produced fluids from a mature well may include a larger fraction of heavier hydrocarbons, for example. As such, sampling produced fluids and determining the presence of heavier hydrocarbons may give information about the condition of the well. Some heavier components of produced fluids may have graphene-like characteristics as described above which may allow the heavier components to be readily detected in the produced fluids. The presence of components with graphene-like characteristics may be correlated with well characteristics as will be described in detail below.

Graphene is a basic unit of all carbon nanostructures. It occupies the seventh position among the most popular nanomaterials used in the oil and gas industry. More specifically, graphene is a nanomaterial which has sufficiently large flakes and described is for its physical properties. Consequently, being a zero-gap semiconductor, and/or a semimetal is one of graphene's characteristic features. Moreover, graphene has a distinctive two-dimensional monolayer stacking of carbon atoms with $sp^2$ hybridization, organized in a flat crystalline network of characteristic hexagonal symmetry. This representative two-dimensional monolayer stacking presents a multitude of benefits. For example, graphene is the only form of carbon, or any other known solid material, in which every atom is available for chemical reaction from two sides. Atoms located at or in proximity to the edges of a graphene sheet may have special chemical reactivity. Consequently, defects within a single sheet of graphene may increase its chemical reactivity. Therefore, graphene may be commonly modified with oxygen and nitrogen-containing functional groups and analyzed by spectroscopic optical signals, changes in core-level binding energies identified by x-ray photoelectron spectroscopy, and conductivity/resistivity electrical measurements. Unique spectroscopic signals may be identifiable with each form of graphene. Furthermore, the structure of graphene and by extension graphene-like structures present unique characteristic signals which may be used to readily identify graphene and graphene-life structures using appropriate instruments. The presence or absence of such characteristic signals may therefore indicate the absence or presence of graphene or graphene-like substances within a subterranean formation and the fluids produced therefrom.

Notably, there is a unique similarity between the stacking mechanism of graphene and certain chemical species in downhole formation fluids. More specifically, certain physical measurements have been demonstrated to reliably identify "graphene" behavior or chemical species with a graphene or graphene-like substrate or backbone structure, wherein this information may be used in a downhole environment to predict certain chemical species that have similar attributes in solution. As will be described in greater detail below, identification of these same chemical species may then be characterized as a function of depth, pressure, temperature, zone, and/or adjacent wells in order to further assist the characterization of reservoir architecture, reservoir continuity and compositional grading, interval productivity, reservoir charging mechanisms, filling histories, and/or migration pathways in a formation reservoir.

In reference to the stacking mechanism of graphene, the first layer may be a graphene hexagonal monolayer. The second layer may be constructed so that the first half of the atoms may be positioned over the center of the hexagon in the bottom layer and the second half of the atoms may be positioned over an atom in the bottom layer. In subsequent layers, the first half of the atoms may be positioned over the hexagon in the second layer, wherein the second half of the atoms may be positioned directly over atoms in the second layer. Optionally, the second half of the atoms may be positioned over atoms in the bottom layer. Repeating this process may result in multiple layers of graphene comprising the same hexagonal crystal structure substrate.

In some embodiments, the graphene or graphene-like substrates may have from at least about 10 to at least about 1,000 stacked sheets. In some embodiments, the graphene or graphene-like substrates may have from at least about 10 to at least about 900 stacked sheets. In some embodiments, the graphene or graphene-like substrates may have from at least about 10 to at least about 800 stacked sheets. In some embodiments, the graphene or graphene-like substrates may have from at least about 10 to at least about 700 stacked sheets. In other embodiments, the graphene or graphene-like substrates may have from at least about 10 up to at least about 600 stacked sheets. In other embodiments, the graphene or graphene-like substrates may have from at least about 10 up to at least about 500 stacked sheets. In other embodiments, the graphene or graphene-like substrates may have from at least about 10 up to at least about 400 stacked sheets. In one embodiment, the graphene-like substrates may have from at least about 10 up to at least about 300 stacked sheets. In other embodiments, the graphene-like substrates may have from at least about 10 up to at least about 200 stacked sheets. In one embodiment, the graphene or graphene-like substrates may have from at least about 10 up to at least about 100 stacked sheets. In some embodiments, the graphene or graphene-like substrates may have from at least about 10 up to at least about 50 sheets, or up to at least about 40 sheets, or up to at least about 25 sheets.

Another unique characteristic of graphene is its linear dispersive dependence of energy on momentum. Hence, electrons in graphene are zero-mass Dirac fermions. In practice, this means high values of thermal and electric conductivity parameters, unique absorption of light, and a number of quantum phenomena. The Young's modulus of graphene is 1.0+/−0.1 TPa, with tensile strength approaching 130+/−10 GPa. As a result, graphene is highly resistant to chemicals, temperature, water and organic solvents.

Embodiments may include a method or system to characterize downhole fluid constituents with a graphene-like substrate in a reservoir formation. As mentioned above, graphene and graphene-like structures may have characteristic signals that may be detected by appropriate instruments. These characteristic signals may be derived from the crystal and electronic structure of graphene and graphene-like materials which may then be used to determine the presence or absence of graphene-like materials within a formation fluid sample which may be used to correlate the fluid to formation characteristics. A formation fluid, i.e. a fluid produced from a subterranean formation, may be sampled in-situ in a wellbore, by a downhole sampling apparatus for example. The sampled fluid may be subjected to various tests which may provoke signals characteristic of graphene and graphene-like materials to be produced from the sample when graphene and graphene-like materials are present. Some tests may include optical measurements using an optical sensor, x-ray measurements using an x-ray sensor, or electrical measurements an electrical sensor. As used herein, the terms "sample" or "sampling" is intended to define fluid collected in a device positioned into the wellbore, whether or not the fluid sample is brought to the surface, and includes the processes of downhole sampling, wellhead sampling, surface recombination sampling, and pump-out operations. The formation fluid may be sampled and measured with a combination of sensors and characterized according to an equation of state and/or thermodynamic models. The measurement may occur downhole, at the surface, or a combination of downhole and surface measurements.

Any of a variety of suitable techniques may be utilized with methods and systems for identifying graphene-like substrates, and ultimately identifying graphene-like gradients. Because graphene has unique spectroscopic signals, a variety of different techniques may be used for identifying graphene-like substrates, wherein the fluid sample may first be analyzed and then correlated to graphene to detect graphene-like substrates. For example, in some embodiments, systems or methods may include the use of optical measurements, including Raman and uV/Vis spectroscopic absorption, and X-ray measurements, including photoelectron spectroscopy. More specifically, comparisons between the optical IR Raman signals and the X-ray photoelectron core binding energy signals of graphene and a formation fluid sample. Graphene and graphene-like structures may exhibit similar or substantially similar characteristics spectrographic signals which may allow ready identification of samples which include graphene and graphene-like structures. In Raman spectroscopy, for example, the inelastic scattering of light from a monochromatic light source may be used to generate a spectrograph of the vibrational modes of molecules within the sample. Graphene and graphene-like materials may have a characteristic peak on the spectrograph produced from Raman spectroscopy as the vibrational modes associates with graphene may be defined by the stacking structure of graphene and graphene-like materials as previously described. For example, a complex polycyclic aromatic hydrocarbon may exhibit spectroscopy signals (characteristic peaks) that are similar to those of graphene. While the specific chemical identity of a complex polycyclic aromatic hydrocarbon may not be completely determined by Raman spectroscopy, the characteristic graphene-like signals associated with the polycyclic aromatic hydrocarbon may allow ready identification that the polycyclic aromatic hydrocarbon is present in the sample. There may be many advantages to detecting a graphene-like signals in a sample such as that as detection of the characteristic signals may quickly allow the presence of the graphene-like material to be confirmed. Correlations about subterranean formation characteristics may then be calculated based on the presence of graphene-like materials in the sample. While the foregoing has discussed Raman spectroscopy in particular, graphene and graphene-like molecules may have characteristic signatures and/or signals that occur in many other tests such as x-ray spectroscopy, infrared spectroscopy, and UV spectroscopy, for example.

Once the sample has been measured and any graphene-like structures have been identified, correlations may be calculated between the fluid sample and characteristics of the subterranean formation. As discussed above, the composition of a produced fluid may vary with well maturity which may result in relatively larger, or smaller, mass fractions of longer chain hydrocarbons to be produced depending on the well maturity. Well maturity may be characterized by an actual lifetime of a well such as when the well was first put into production, a total volume of fluid produced by the wellbore, or a combination thereof. A subterranean formation may include multiple wells that drain from different regions of the subterranean formation. As subterranean formations may include stratified layers of similar materials, regions of a subterranean formation may have similar properties even when the regions are physically distant. Since a first region of a subterranean formation may have similar characteristics as a second region of the subterranean formation, inferences may be drawn about the characteristics of the second region based at least in part on characteristics of the second region. For example, wells positioned within the same formation may be expected to have similar characteristics in the composition of produced fluids over the lifetime of the well. The presence and concentration of graphene-like materials in produced fluids from a first well may be recorded and stored in a database, for example. A concentration of graphene-like materials produced from a second well may be analyzed and correlated to the production of graphene like-materials from the first well. The results of the correlation may give information as to the maturity of the well and expected composition of produced fluids, for example. Detecting a graphene-like structure within produced fluids from one well may allow a correlation to be calculated regarding subterranean formation properties. The correlation may be based at least in part on historical data gathered from wells in the same formation, similar formations, or from subterranean formations with similar lithography, for example. Detection of graphene like structures may also allow correlation to reservoir characteristics.

Some reservoir characteristics that may be correlated using the techniques described herein may include reservoir architecture. Reservoir architecture may include information that describes the geometry of a producing zone within a subterranean formation. Such information may include, but is not limited to, trap configuration, seal capacity, and base of the producing zone. Another reservoir characteristic that may be correlated using the techniques described herein may include interval productivity. Interval productivity may be information related to the rate of production of formation fluids over time, for example. Historical production data may be correlated with a concentration of graphene-like materials from the produced fluids. Then, with a measured concentration of graphene-like materials detected in a fluid sample, the correlation may be used to estimate the future production based at least in part on the correlation. Another reservoir characteristic that may be correlated using the techniques described herein may include reservoir charging mechanisms such as water migration and accumulation of hydrocarbons within producing zones. Another reservoir characteristic that may be correlated using the techniques described herein may include reservoir filling history which may include information about how the reservoir came to be a producing reservoir. Reservoir filling history may give information about the kind of hydrocarbons present in the formation, for example. Yet another reservoir characteristic that may be correlated using the techniques described herein may include reservoir migration pathways.

Some embodiments may include a system or method to characterize downhole fluid constituents with a graphene-like substrate in a reservoir formation, wherein a formation fluid may be sampled and measured with a combination of sensors and characterized according to an equation of state and/or thermodynamic models. Reservoir architecture may be determined by characterizing the properties of formation fluid constituents exhibiting a graphene-like substrate with respect to sampling depth, pressure, temperature, and/or adjacent wells. Any of a variety of sensors may be used in the analysis. Such sensors may include, but are not limited to an optical sensor, an x-ray sensor, or an electrical sensor. For example, the embodiments may include a system or method to characterize downhole fluid constituents with a graphene-like substrate in a reservoir formation, wherein the formation fluid may be sampled in-situ and measured with an optical sensor. embodiments may also include sampling of the formation fluid in-situ and measuring with an x-ray sensor. The embodiments may further include sampling of the formation fluid in-situ and measuring with an electrical sensor. Combinations of these sensors may be used.

Figure 1A:
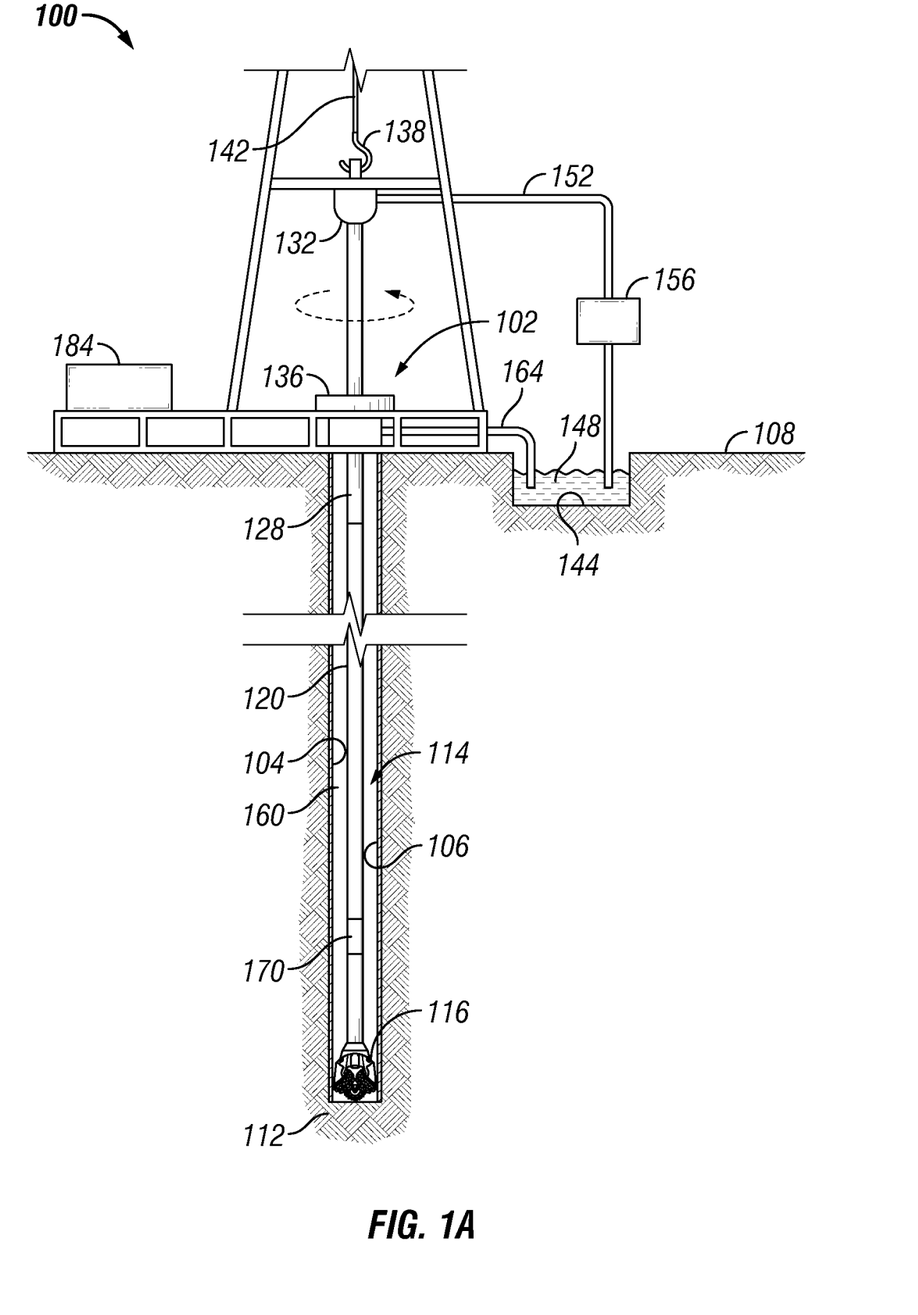
FIG. 1A illustrates a schematic view of a well in which an example embodiment of a fluid sample system is deployed.

FIG. 1A illustrates a fluid sampling system 100 according to an illustrative embodiment used in a well 102 having a wellbore 104 that extends from a surface 108 of the well 102 to or through a subterranean formation 112. While the wellbore 104 is shown extending generally vertically into the subterranean formation 112, the principles described herein may also applicable to wellbores that extend at an angle through the subterranean formations 112, such as horizontal and slanted wellbores. For example, although FIG. 1A shows wellbore 104 that is vertical or low inclination, high inclination angle or horizontal placement of the wellbore 104 and equipment is also possible. In addition, it should be noted that while FIG. 1A generally depicts a land-based operation, those skilled in the art should readily recognize that the principles described herein are equally applicable to subsea operations that employ floating or sea-based platforms and rigs, without departing from the scope of the disclosure.

The well 102 is illustrated with the fluid sampling system 100 being deployed in a drilling assembly 114. In the embodiment illustrated in FIG. 1A, the well 102 is formed by a drilling process in which a drill bit 116 is turned by a drill string 120 that extends from the drill bit 116 to the surface 108 of the well 102. The drill string 120 may be made up of one or more connected tubes or pipes, of varying or similar cross-section. The drill string 120 may refer to the collection of pipes or tubes as a single component, or alternatively to the individual pipes or tubes that comprise the string. The term "drill string" is not meant to be limiting in nature and may refer to any component or components that are capable of transferring rotational energy from the surface of the well to the drill bit. In several embodiments, the drill string 120 may include a central passage disposed longitudinally in the drill string 120 and capable of allowing fluid communication between the surface 108 of the well 102 and downhole locations.

At or near the surface 108 of the well 102, the drill string 120 may include or be coupled to a kelly 128. The kelly 128 may have a square, hexagonal, octagonal, or other suitable cross-section. The kelly 128 may be connected at one end to the remainder of the drill string 120 and at an opposite end to a rotary swivel 132. As illustrated, the kelly 120 may pass through a rotary table 136 that may be capable of rotating the kelly 128 and thus the remainder of the drill string 120 and drill bit 116. The rotary swivel 132 may allow the kelly 128 to rotate without rotational motion being imparted to the rotary swivel 132. A hook 138, cable 142, traveling block (not shown), and hoist (not shown) may be provided to lift or lower the drill bit 116, drill string 120, kelly 128 and rotary swivel 132. The kelly 128 and swivel 132 may be raised or lowered as needed to add additional sections of tubing to the drill string 120 as the drill bit 116 advances, or to remove sections of tubing from the drill string 120 if removal of the drill string 120 and drill bit 116 from the well 102 may be desired.

A reservoir 144 may be positioned at the surface 108 and holds drilling fluid 148 for delivery to the well 102 during drilling operations. A supply line 152 may fluidly couple the reservoir 144 and the inner passage of the drill string 120. A pump 156 may drive the drilling fluid 148 through the supply line 152 and downhole to lubricate the drill bit 116 during drilling and to carry cuttings from the drilling process back to the surface 108. After traveling downhole, the drilling fluid 148 may return to the surface 108 by way of all annulus 160 formed between the drill string 120 and the wellbore 104. At the surface 108, the drilling mud 148 may be returned to the reservoir 144 through a return line 164. The drilling mud 148 may be filtered or otherwise processed prior to recirculation through the well 102.

Figure 1B:
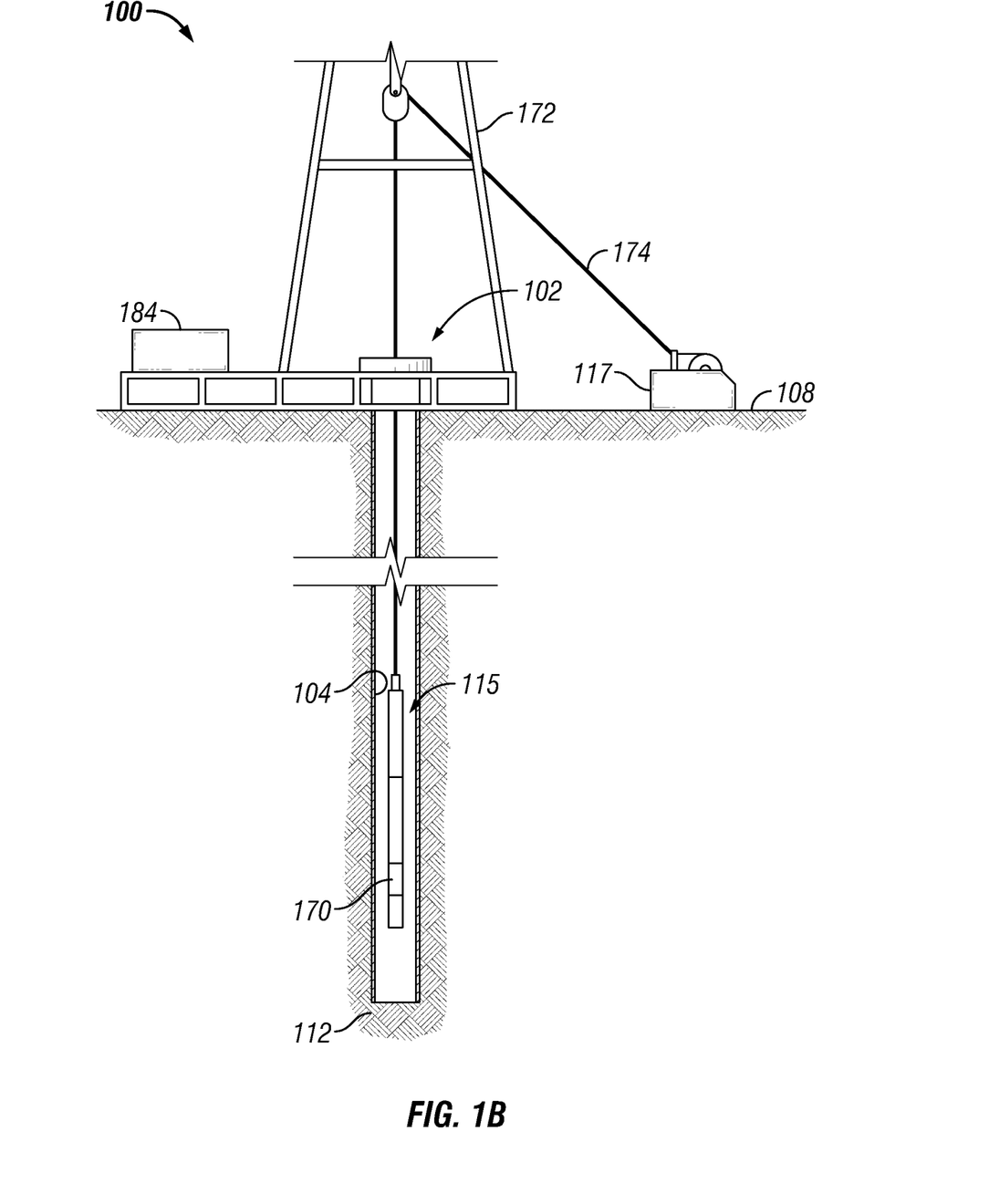
FIG. 1B illustrates a schematic view of another well in which an example embodiment of a fluid sample system is deployed.

FIG. 1B illustrates a schematic view of another embodiment of well 102 in which an example embodiment of fluid analysis system 100 may be deployed. As illustrated, fluid analysis system 100 may be deployed as part of a wireline assembly 115, either onshore of offshore. As illustrated, the wireline assembly 115 may include a winch 117, for example, to raise and lower a downhole portion of the wireline assembly 115 into the well 102. As illustrated, fluid analysis system 100 may include fluid sampling tool 170 attached to the winch 117. Fluid sampling tool 170 may or may not be attached to a winch unit 104. Fluid sampling tool 170 may be supported by rig 172 at surface 108.

Fluid sampling tool 170 may be tethered to the winch 117 through wireline 174. While FIG. 1B illustrates wireline 174, it should be understood that other suitable conveyances may also be used for providing mechanical conveyance to fluid sampling tool in the well 102, including, but not limited to, slickline, coiled tubing, pipe, drill pipe, drill string, downhole tractor, or the like. In some examples, the conveyance may provide mechanical suspension, as well as electrical connectivity, for fluid sampling tool 170. Wireline 174 may comprise, in some instances, a plurality of electrical conductors extending from winch 117. By way of example, wireline 174 may comprise an inner core of seven electrical conductors (not shown) covered by an insulating wrap. An inner and outer steel armor sheath may be wrapped in a helix in opposite directions around the conductors. The electrical conductors may be used for communicating power and telemetry downhole to fluid sampling tool 170.

With reference to both FIGS. 1A and 1B, operation of fluid sampling tool 170 for sample collection will now be described in accordance with example embodiments. Fluid sampling tool 170 may be raised and lowered into well 102 on drill string 120 (FIG. 1A) and wireline 174. (FIG. 1B). Fluid sampling tool 170 may be positioned downhole to obtain fluid samples from the subterranean formation 112 for analysis. The fluid sampling tool 170 may be operable to measure, process, and communicate data regarding the subterranean formation 112, fluid from the subterranean formation 112, or other operations occurring downhole. After recovery, the fluid sample may be analyzed, using any appropriate techniques for detecting graphene and/or graphene-like materials by detecting a characteristic signal associated with graphene. A correlation may be applied as described above determine one or more characteristics of the subterranean formation.

In some embodiments, the data measured and collected by the fluid sampling tool 170 may include, without limitation, pressure, temperature, flow, acceleration (seismic and acoustic), and strain data. As described in more detail below, the fluid sampling tool 170 may include a communications subsystem, including a transceiver for communicating using mud pulse telemetry or another suitable method of wired or wireless communication with a surface controller 184. The transceiver may transmit data gathered by the fluid sampling tool 170 or receive instructions from a well operator via the surface controller 184 to operate the fluid sampling tool 170.

Figure 2:
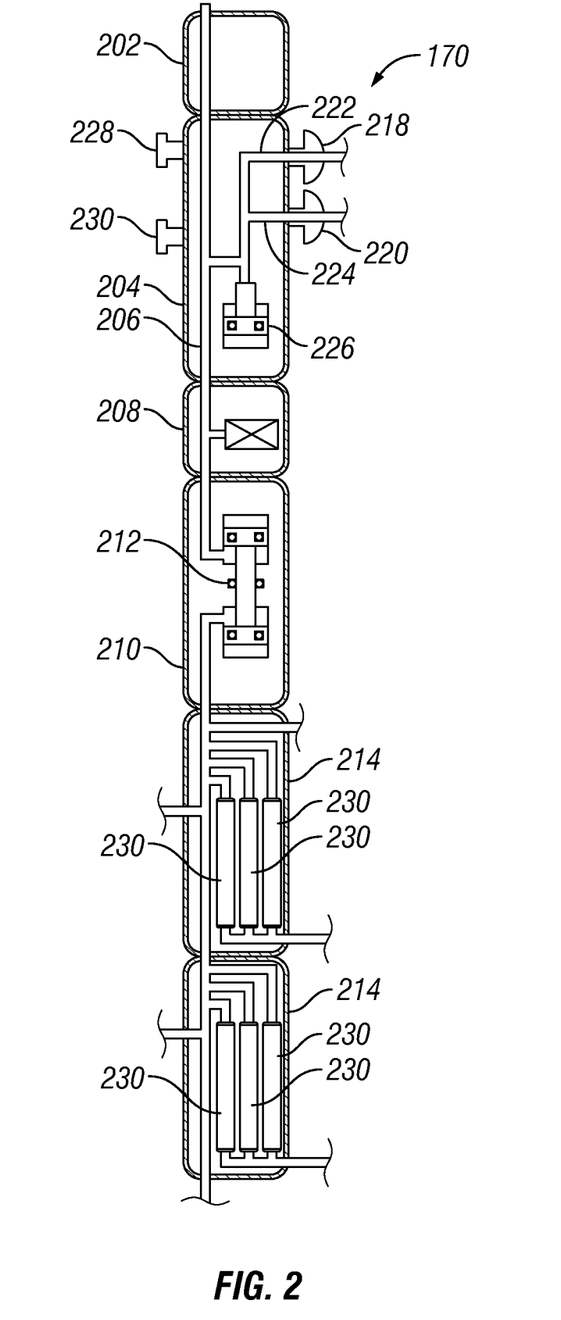
FIG. 2 illustrates a schematic view of an example embodiment of a fluid sampling tool.

Referring now to FIG. 2, an example embodiment of a fluid sampling tool 170 is illustrated as a tool for gathering fluid samples from a formation for subsequent analysis and testing. It should be understood that the fluid sampling tool 170 shown on FIG. 2 is merely illustrative and the example embodiments disclosed herein may be used with other tool configurations. In an embodiment, the fluid sampling tool 170 includes a transceiver 202 through which the fluid sampling tool 170 may communicate with other actuators and sensors in a conveyance, the conveyance's communications system, and with a surface controller (surface controller 184 on FIG. 1A). In an embodiment, the transceiver 202 may also be the port through which various actuators (e.g. valves) and sensors (e.g., temperature and pressure sensors) in the fluid sampling tool 170 are controlled and monitored by, for example, a computer in another part of the conveyance or by the surface controller 184. In an embodiment, the transceiver 202 may include a computer that exercises the control and monitoring function.

The fluid sampling tool 170 may include a dual probe section 204, which may extract fluid from the formation (e.g., formation 112 on FIGS. 1A and 1B), as described in more detail below, and may deliver it to a channel 206 that extends from one end of the fluid sampling tool 170 to the other. The channel 206 may be connected to other tools or portions of the fluid sampling tool 170 arranged in series. The fluid sampling tool 170 may also include a gauge section 208, which may include sensors to allow measurement of properties, such as temperature and pressure, of the fluid in the channel 206. The fluid sampling tool 170 may also include a flow control pump-out section 210, which may include a pump 212 for pumping fluid through the channel 206. The fluid sampling tool 170 may also include one or more chambers such as multi-chamber sections 214, which are described in more detail below.

In some embodiments, the dual probe section 204 may include two probes 218, 220 which may extend from the fluid sampling tool 170 and may press against the borehole wall to receive fluid for sampling. Probe channels 222, 224 may connect the probes 218, 220 to the channel 206. The pump 212 may be used to pump fluids from the reservoir, through the probe channels 222, 224 and to the channel 206. Alternatively, a low volume pump 226 may be used for this purpose. Two standoffs or stabilizers 228, 230 may be used to hold the fluid sampling tool 170 in place as the probes 218, 220 may press against the borehole wall to receive fluid. In an embodiment, the probes 213, 220 and stabilizers 223, 230 may be retracted when the tool is in motion and may be extended to gather samples of fluid from the formation.

Figure 3:
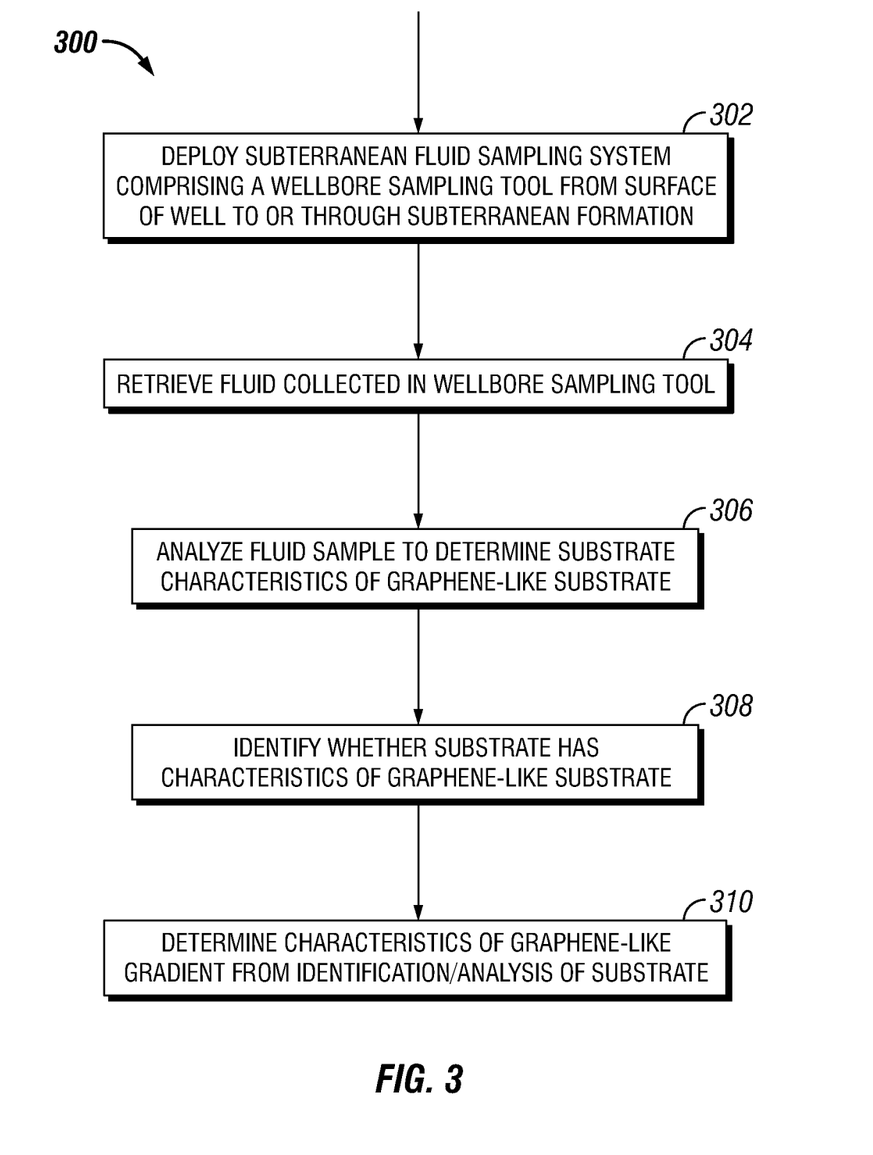
FIG. 3 is a flow chart illustrating an example of a method of detection of a graphene-like substrate.

Referring to FIG. 3, flow chart 300 illustrates an example of a method of detection, analysis, determination presence and/or concentration of a graphene-like material within a sample. The method may begin with step 302. In step 302, a subterranean fluid sampling system comprising a wellbore sampling tool may be deployed from a surface of a well down through a subterranean formation to collect at least one sample of formation fluid. The method may further include step 304. In step 304, the sample may be retrieved or otherwise collected in the wellbore sampling tool. In a surface embodiment, the retrieval may occur at a surface of the wellbore, for example. The formation fluid sample may then be analyzed in step 306 using any of the previously described techniques, such as Raman spectroscopy, to determine whether the collected sample exhibits graphene-like characteristic signals and/or a concentration thereof. After analyzing in step 306, a correlation may be applied as described above to determine one or more subterranean formation characteristics such as reservoir architecture, interval productivity, reservoir charging mechanisms, reservoir filling history, reservoir migration pathways, or combinations thereof at step 310.

In some embodiments, the formation characteristic determined in step 310 may include reservoir architecture. Any suitable technique may be used for correlated detection of graphene-like substrates with reservoir architecture. For example, consider a subterranean well drilled through isolated reservoir compartments. In such a case, the formation characteristic correlated to the graphene-like substrate gradient may be ill-defined or may not demonstrate a correlation to depth. Hence, this correlation may be established with a trend line as a function of depth, or a more complex correlation model may comprise equation of state models or other ancillary sensor inputs. This may indicate that the reservoir architecture may be compartmentalized and may be contrasted with a reservoir architecture in which a clear correlation of the measured characteristic with depth may be expected.

In some embodiments, the formation characteristic determined in step 310 may include interval productivity and reservoir filling history. Any suitable technique may be used for correlated detection of graphene-like substrates with interval productivity. For example, if the measured characteristic in step 310 yields different properties, composition, or characteristics for similar depths and/or pressures, this data may be modeled and correlated with a reservoir that may have an immature filling history or that may not equilibrated and therefore may have a low productivity.

In some embodiments, the formation characteristic determined in step 310 may include reservoir migration pathways. Any suitable technique may be used for correlated detection of graphene-like substrates with reservoir migration pathways. Similar to the reservoir architecture example, the reservoir migration pathway may be ascertained by obtaining measurements of the graphene-like substrate samples at various locations both as a function of depth and multiple wells drilled in close proximity to each other. If, for example, a correlation exists and may be established between the different measurement locations and the measured property, the reservoir migration pathway may be further realized.

Figure 4:
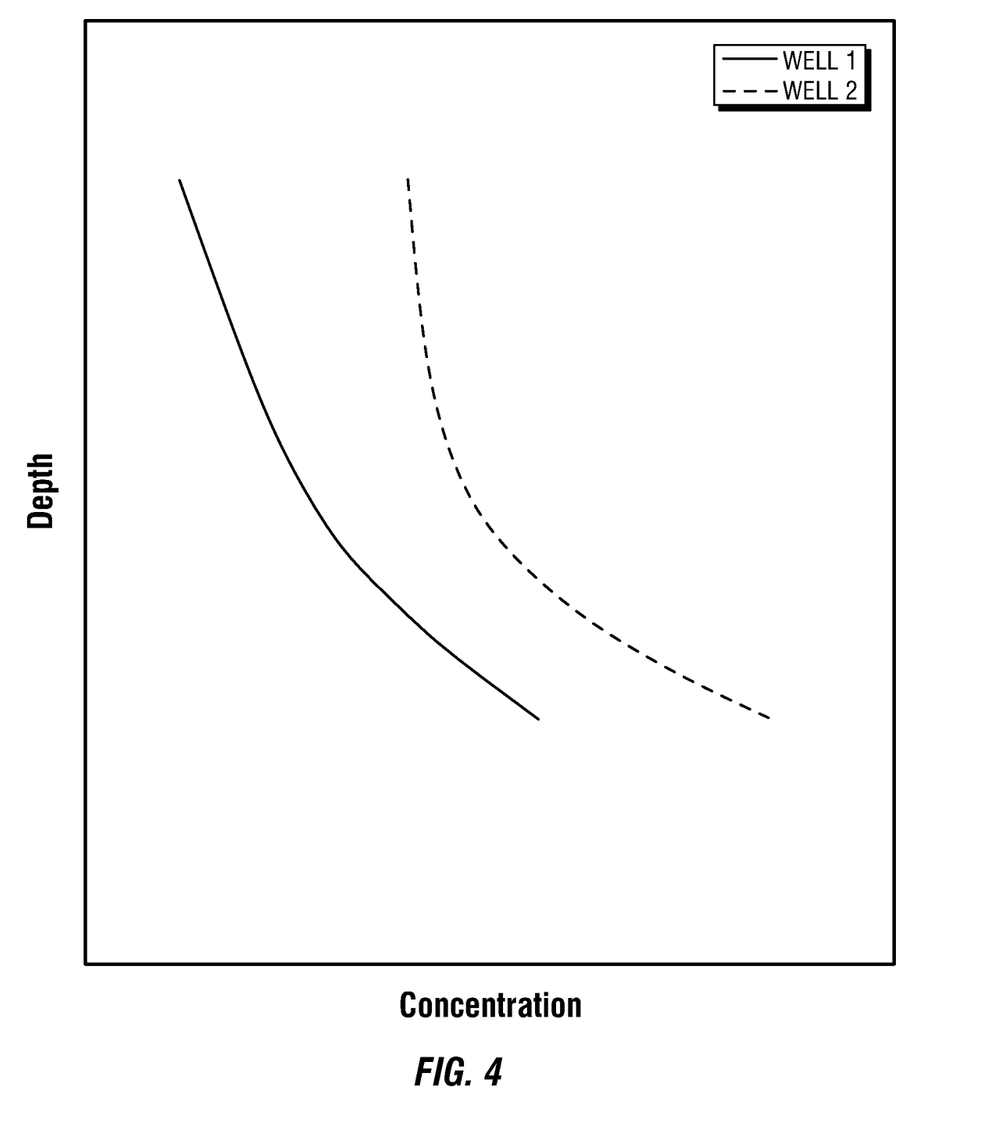
FIG. 4 illustrates a graphical depiction of depth versus concentration measurements used to predict stacking structure of subterranean substrates.

FIG. 4 illustrates an exemplary embodiment depicting a graphical representation of spectroscopic testing in relation to a graphene-like signature to indicate detection of a graphene-like substrate from which information about reservoir architecture and compartmentalization may be ascertained. As shown in FIG. 4, "Well 1", a first subterranean well, may be drilled to a given depth at one location at a well site. At certain depths along the well bore, a sample fluid may be extracted from the reservoir such that a spectroscopic measurement may be performed on a representative formation fluid. The spectrum may be analyzed to extract information specific to a graphene-like spectroscopic peak. In particular, a certain resonant spectroscopic peak may exist at a given wavelength unique to graphene-like substrates.

For example, the resonant spectroscopic peak may be at least ~2700 $cm^{-1}$ for a Raman shift, or at least 18 284 eV binding energy for X-ray photoelectron spectroscopy. The resonant spectroscopic peak for a Raman shift may be at least about 2700 $cm^{-1}$, at least about 2800 $cm^{-1}$, at least about 2900 $cm^{-1}$, at least about 3000 $cm^{-1}$, or at least about 3400 $cm^{-1}$; or from at least about 2700 $cm^{-1}$ up to at least about 3400 $cm^{-1}$, or from at least about 2800 $cm^{-1}$ up to at least about 300 $cm^{-1}$. The binding energy for X-ray photoelectron spectroscopy may be at least about 284 eV, at least about 286 eV, at least about 288 eV, at least about 290 eV, or at least about 300 eV; or from at least about 284 eV up to at least about 300 eV. In the absence of the resonant spectroscopic feature, one skilled in the art may conclude the reservoir sample may not contain a graphene-like substrate material. In addition, if the resonant feature is present, the amplitude or height of the peak may correlate to the relative quantity or concentration present of the sample responsible for the unique spectroscopic resonant feature. Multiple spectroscopic measurements may then be made at different depths/locations along the well bore to identify: 1) if a unique graphene-like spectroscopic resonance exists, and 2) the relative height, amplitude, or concentration present. A normalized value of this relative height, amplitude, or concentration may then be plotted as a function of concentration (x-axis) versus depth (y-axis) to correlate the distribution of the graphene-like substrate material within the reservoir. Moreover, as depicted in FIG. 4, "Well 2", a second subterranean well, may be drilled at a different location, such as, for example, 1 km away from the first subterranean well. A fluid sampling and spectroscopic analysis, as a function of concentration versus depth, may then be performed for Well 2, similar to the analysis of Well 1. The differences between these two trends may then be used to develop a model or correlation of the reservoir architecture.

In some embodiments of the present invention, a method or system for detecting graphene-like substrates may include detecting the total concentration of gas-liquid molecules, with knowledge of the chemical environment. For example, the method may include performing measurements at various depths, then predicting the stacking structure of the substrates based on the total concentration and chemical environment as a function of depth, then measuring the stacking structure of the substrate. The method may further include determining a gradient model after predicting the stacking structure of the substrate. Additionally, the method may further include determining components derived from the gradient information.

Accordingly, this disclosure describes methods and systems determining the presence of graphene or graphene-like substrates or gradients in subterranean formations. Without limitation, the methods and systems may further be characterized by one or more of the following statements:

Statement 1. A method may comprise sampling a wellbore fluid; analyzing the wellbore fluid and determining a presence of a graphene-like substrate, a concentration of the graphene-like substrate, or both, in the wellbore fluid; and correlating the presence and the concentration of the graphene-like substrate to at least one subterranean formation characteristic.

Statement 2. The method of statement 1, wherein sampling the wellbore fluid comprises sampling in a wellbore using a wellbore sampling tool.

Statement 3. The method of statement 1 or 2, wherein sampling the wellbore fluid comprises sampling at a surface of the wellbore by pumping the wellbore fluid out of the wellbore.

Statement 4. The method of any one of the preceding statements, wherein determining a presence of the graphene-like substrate comprises detecting a characteristic signal of graphene-like substrates.

Statement 5. The method of statement 4, wherein the characteristic signal is a spectrographic peak.

Statement 6. The method of statement 5, wherein the spectrographic peak is at least about 2700 cm$^{-1}$ for a Raman shift.

Statement 7. The method of statement 5, wherein the spectrographic peak is at least about 284 eV binding energy for X-ray photoelectron spectroscopy.

Statement 8. The method of any one of the preceding statements, wherein the at least one subterranean formation characteristic comprises at least one of reservoir architecture, interval productivity, reservoir charging mechanisms, reservoir filling history, reservoir migration pathways, or combinations thereof.

Statement 9. The method of statement 8, wherein the reservoir architecture comprises at least one of trap configuration, seal capacity, a base of a producing zone, or combinations thereof.

Statement 10. The method of any one of the preceding statements, wherein the presence of the graphene-like substrate is determined as a function of depth.

Statement 11. The method of any of the preceding statements, wherein the graphene-like substrate comprises from at least about 10 up to at least about 1,000 stacked layers.

Statement 12. The method of any of the preceding statements, wherein the graphene-like substrate comprises from at least about 10 up to at least about 500 stacked layers.

Statement 13. The method of any of the preceding statements, wherein the graphene-like substrate comprises from at least about 10 up to at least about 100 stacked layers.

Statement 14. The method of any one of statements 11 to 13, wherein the stacked layers comprise a hexagonal crystal structure substrate.

Statement 15. The method of any one of the preceding statements, wherein determining a presence of the concentration of the graphene-like substrate comprises detecting a total concentration of gas-liquid molecules and performing measurements at various depths.

Statement 16. The method of statement 15, further comprising predicting a stacking structure of the graphene-like substrate based on the total concentration of gas-liquid molecules and chemical environment as a function of depth, then measuring the stacking structure of the graphene-like substrate.

Statement 17. The method of statement 15, or 16, further comprising determining a gradient model after predicting the stacking structure of the graphene-like substrate.

Statement 18. The method of any one of statements 15 to 17, further comprising determining components derived from the gradient model.

Statement 19. A system may comprise a wellbore sampling tool, wherein the wellbore sampling tool is used to sample a wellbore fluid; and a spectrographic analysis, wherein the spectrographic analysis comprises: analyzing the wellbore fluid and determining a presence of a graphene-like substrate, a concentration of the graphene-like substrate, or both, in the wellbore fluid; and correlating the presence and the concentration of the graphene-like substrate to at least one subterranean formation characteristic.

Statement 20. The system of statement 19, wherein the at least one subterranean formation characteristic comprises at least one of reservoir architecture, interval productivity, reservoir charging mechanisms, reservoir filling history, reservoir migration pathways, or combinations thereof.

The preceding description provides various embodiments of the systems and methods of use disclosed herein which may contain different method steps and alternative combinations of components. It should be understood that, although individual embodiments may be discussed herein, the present disclosure covers all combinations of the disclosed embodiments, including, without limitation, the different component combinations, method step combinations, and properties of the system. It should be understood that the compositions and methods are described in terms of "including," "containing," or "including" various components or steps, the compositions and methods can also "consist essentially of" or "consist of" the various components and steps. Moreover, the indefinite articles "a" or "an," as used in the claims, are defined herein to mean one or more than one of the elements that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only and may be modified and practiced in different but equivalent manners apparent to those skilled in the art having the benefit of the teachings herein. Although individual embodiments are discussed, the disclosure covers all combinations of all of the embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of those embodiments. If there is any conflict in the usages of a word or term in this specification and one or more patent(s) or other documents that may be incorporated herein by reference, the definitions that are consistent with this specification should be adopted.

What is claimed is:

1. A method comprising:
sampling a wellbore fluid;
analyzing the wellbore fluid and determining a presence of a graphene-like substrate, a concentration of the graphene-like substrate, or both, in the wellbore fluid; and
correlating the presence and the concentration of the graphene-like substrate to at least one subterranean formation characteristic.

2. The method of claim 1, wherein sampling the wellbore fluid comprises sampling in a wellbore using a wellbore sampling tool.

3. The method of claim 1, wherein sampling the wellbore fluid comprises sampling at a surface of the wellbore by pumping the wellbore fluid out of the wellbore.

4. The method of claim 1, wherein determining a presence of the graphene-like substrate comprises detecting a characteristic signal of graphene-like substrates.

5. The method of claim 4, wherein the characteristic signal is a spectrographic peak.

6. The method of claim 5, wherein the spectrographic peak is at least about 2700 $cm^{-1}$ for a Raman shift.

7. The method of claim 5, wherein the spectrographic peak is at least about 284 eV binding energy for X-ray photoelectron spectroscopy.

8. The method of claim 1, wherein the at least one subterranean formation characteristic comprises at least one of reservoir architecture, interval productivity, reservoir charging mechanisms, reservoir filling history, reservoir migration pathways, or combinations thereof.

9. The method of claim 8, wherein the reservoir architecture comprises at least one of trap configuration, seal capacity, a base of a producing zone, or combinations thereof.

10. The method of claim 1, wherein the presence of the graphene-like substrate is determined as a function of depth.

11. The method of claim 1, wherein the graphene-like substrate comprises from at least about 10 up to at least about 1,000 stacked layers.

12. The method of claim 11, wherein the graphene-like substrate comprises from at least about 10 up to at least about 500 stacked layers.

13. The method of claim 12, wherein the graphene-like substrate comprises from at least about 10 up to at least about 100 stacked layers.

14. The method of claim 13, wherein the stacked layers comprise a hexagonal crystal structure substrate.

15. The method of claim 1, wherein determining a presence of the concentration of the graphene-like substrate comprises detecting a total concentration of gas-liquid molecules and performing measurements at various depths.

16. The method of claim 15, further comprising predicting a stacking structure of the graphene-like substrate based on the total concentration of gas-liquid molecules and chemical environment as a function of depth, then measuring the stacking structure of the graphene-like substrate.

17. The method of claim 16, further comprising determining a gradient model after predicting the stacking structure of the graphene-like substrate.

18. The method of claim 17, further comprising determining components derived from the gradient model.

* * * * *

UNITED STATES PATENT AND TRADEMARK OFFICE
CERTIFICATE OF CORRECTION

| | | |
|---|---|---|
| PATENT NO. | : 11,231,407 B2 | Page 1 of 1 |
| APPLICATION NO. | : 16/578559 | |
| DATED | : January 25, 2022 | |
| INVENTOR(S) | : Price et al. | |

It is certified that error appears in the above-identified patent and that said Letters Patent is hereby corrected as shown below:

In the Specification

Column 9 Lines 1-2:
Please replace "the probes 213,220 and stabilizers 223, 230" with --the probes 218, 220, and stabilizers 223, 230--

Column 10 Line 14:
Please replace "for a Raman shift, or at least 18 284 eV" with --for a Raman shift, or at least ~284 eV--

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*